United States Patent
Zharotia

(10) Patent No.: US 10,691,650 B2
(45) Date of Patent: Jun. 23, 2020

(54) METHOD AND SERVER FOR VENDOR-INDEPENDENT ACQUISITION OF MEDICAL DATA

(71) Applicant: Wipro Limited, Bangalore (IN)

(72) Inventor: Vijay Kumar Zharotia, Bangalore (IN)

(73) Assignee: Wipro Limited, Bangalore (IN)

(*) Notice: Subject to any disclaimer, the term of this patent is extended or adjusted under 35 U.S.C. 154(b) by 559 days.

(21) Appl. No.: 15/358,309

(22) Filed: Nov. 22, 2016

(65) Prior Publication Data
US 2018/0060502 A1 Mar. 1, 2018

(30) Foreign Application Priority Data
Sep. 1, 2016 (IN) .............................. 201641029903

(51) Int. Cl.
| | |
|---|---|
| H04L 29/08 | (2006.01) |
| G06F 16/21 | (2019.01) |
| G16H 40/63 | (2018.01) |
| G16H 10/60 | (2018.01) |
| G16H 10/20 | (2018.01) |
| G16H 40/67 | (2018.01) |

(52) U.S. Cl.
CPC ............. *G06F 16/21* (2019.01); *G16H 10/20* (2018.01); *G16H 10/60* (2018.01); *G16H 40/63* (2018.01); *G16H 40/67* (2018.01); *H04L 67/1097* (2013.01); *H04L 67/14* (2013.01)

(58) Field of Classification Search
CPC ........ G16H 50/20; G16H 50/70; G16H 50/50; G16H 20/10; G16H 10/60; G16H 10/40; G16H 20/17; G06Q 10/063; G06Q 10/0633; A61N 1/37247; G06F 19/34; G06F 17/5009; G06F 19/00; G06K 19/0723; G06K 19/07309; G06K 7/0008; G06K 7/10198; G06K 17/0022; G06K 19/07749; G06K 7/10009; G06K 7/10158; H01Q 1/2225; H01Q 1/38
See application file for complete search history.

(56) References Cited

U.S. PATENT DOCUMENTS

| | | |
|---|---|---|
| 7,685,006 B2 | 3/2010 | Riff et al. |
| 2005/0021519 A1 | 1/2005 | Ghouri |
| 2010/0286997 A1 | 11/2010 | Srinivasan |

(Continued)

*Primary Examiner* — Maroun P Kanaan
(74) *Attorney, Agent, or Firm* — Finnegan, Henderson, Farabow, Garrett & Dunner, LLP

(57) ABSTRACT

The present disclosure relates to server and a method for vendor-independent acquisition of medical data by healthcare units. The method comprises transmitting request to a cloud database by the server at predefined intervals of time. The request comprise list of one or more medical devices associated with one or more subjects of the health care unit. Further, the server obtains medical data of the one or more subjects from the cloud database based on the request and correlation of the medical data with medical device data. Upon receiving the medical data, Device Message Layer (DML) communication session is established with a data manager of the health care unit by the server and the medical data is transmitted to the data manager through the established DML communication session by the server for vendor-independent acquisition of the medical data by health care units.

12 Claims, 7 Drawing Sheets

(56) References Cited

U.S. PATENT DOCUMENTS

| | | | |
|---|---|---|---|
| 2013/0231947 A1* | 9/2013 | Shusterman | G06F 19/3418 705/2 |
| 2014/0046695 A1 | 2/2014 | Meyer | |
| 2014/0062900 A1* | 3/2014 | Kaula | A61N 1/37247 345/173 |
| 2017/0011105 A1* | 1/2017 | Shet | G06Q 10/00 |

* cited by examiner

METHOD AND SERVER FOR VENDOR-INDEPENDENT ACQUISITION OF MEDICAL DATA

FIELD OF THE DISCLOSURE

The present subject matter generally relates to field of health care. More particularly, but not exclusively, the present disclosure discloses a server and a method for vendor-independent acquisition of the medical data by the health care units.

BACKGROUND

Evolution of health care systems has brought about tremendous need in advancements of technology related to the health care systems, Point of Care Testing (POCT) in the health care systems are medical diagnostic testing performed on a subject by implementing POCT devices also referred as medical devices in any health care units such as clinical laboratories or hospitals where the subject is receiving care or treatment, POCT may be performed by non-laboratory personnel and results of the POCT are stored and used for clinical decision making at the health care units. In a system where multiple POCT devices are configured to perform testing of one or more subjects, each of the multiple POCT devices is integrated with the health care unit, which acquires the results of the POCT through a data manager. The integration includes establishing POC Result Generator (POCRG) interface at each of the multiple POCT devices for the acquisition. In one embodiment, the POCRG interface is defined in POCT1-A2 standard with a set of standard messages using HL7 messages exchanged between the data manager and the POCT devices. The set of standardized messages make the POCRG interface vendor independent for acquisition of the POCT results or medical data of the associated subject.

Further, integration of POCT in home setting of subjects, i.e., when the POCT devices are located at a different location other than the health care unit premises, with the data manager of the health care unit involves a complex network. As described, the POCRG interface should be established with each of the said POCRG and the data manager. Also, in the POCT devices may be manufactured by different vendors and therefore there may be a need for establishing the POCRG interface with each of the POCT devices belonging to different vendors. Further, upon the acquisition of the medical data or the results, mapping of the medical data with a unique subject ID associated with each of the corresponding subject must be performed. Furthermore, acquiring and storing the medical data against an order based on request of the health care units may be a challenge. Also, huge effort and maintenance support may be required for the mapping and storing the medical data for an order. Overall, existing systems for acquisition of the medical data involves vendor support and large integration effort for establishing the POCRG interface for each of the vendor.

SUMMARY

Disclosed herein is a method for vendor-independent acquisition of medical data by health care units. The method comprises the server initially transmitting request to a cloud database at predefined intervals of time. Here, the request comprises list of one or more medical devices associated with one or more subjects of the health care unit. Further, the server obtains medical data of the one or more subjects from the cloud database based on the request and correlation of the medical data with medical device data. Here, the correlation is performed by the cloud database and the medical data is received by the cloud database from one or more user devices associated with the one or more subjects. Upon receiving the medical data, the server establishes a Device Message Layer (DML) communication session with a data manager of the health care unit and transmits the medical data to the data manager through the established DML communication session for vendor-independent acquisition of the medical data by health care units.

Embodiments of present disclosure disclose a server for vendor-independent acquisition of medical data by health care units. The server comprises a processor and a memory communicatively coupled to the processor. The memory stores processor-executable instructions which on execution cause the processor to transmit request to a cloud database at predefined intervals of time, wherein the request comprise list of one or more medical devices associated with one or more subjects of the health care unit. Further, the processor obtains medical data of the one or more subjects from the cloud database based on the request and correlation performed by a cloud database. The correlation is of the medical data with medical device data. Here, the medical data is received by the cloud database from one or more user devices associated with the one or more subjects. Further, the processor is configured to establish a Device Message Layer (DML) communication session with a data manager of the health care unit upon receiving the medical data and transmit the medical data to the data manager through the established DML communication session for vendor-independent acquisition of the medical data by health care units.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The accompanying drawings, which are incorporated in and constitute a part of this disclosure, illustrate exemplary embodiments and, together with the description, serve to explain the disclosed principles. In the figures, the left-most digit(s) of a reference number identifies the figure in which the reference number first appears. The same numbers are used throughout the figures to reference like features and components. Some embodiments of system and/or methods in accordance with embodiments of the present subject matter are now described, by way of example only, and with reference to the accompanying figures, in which.

Figure 1A:
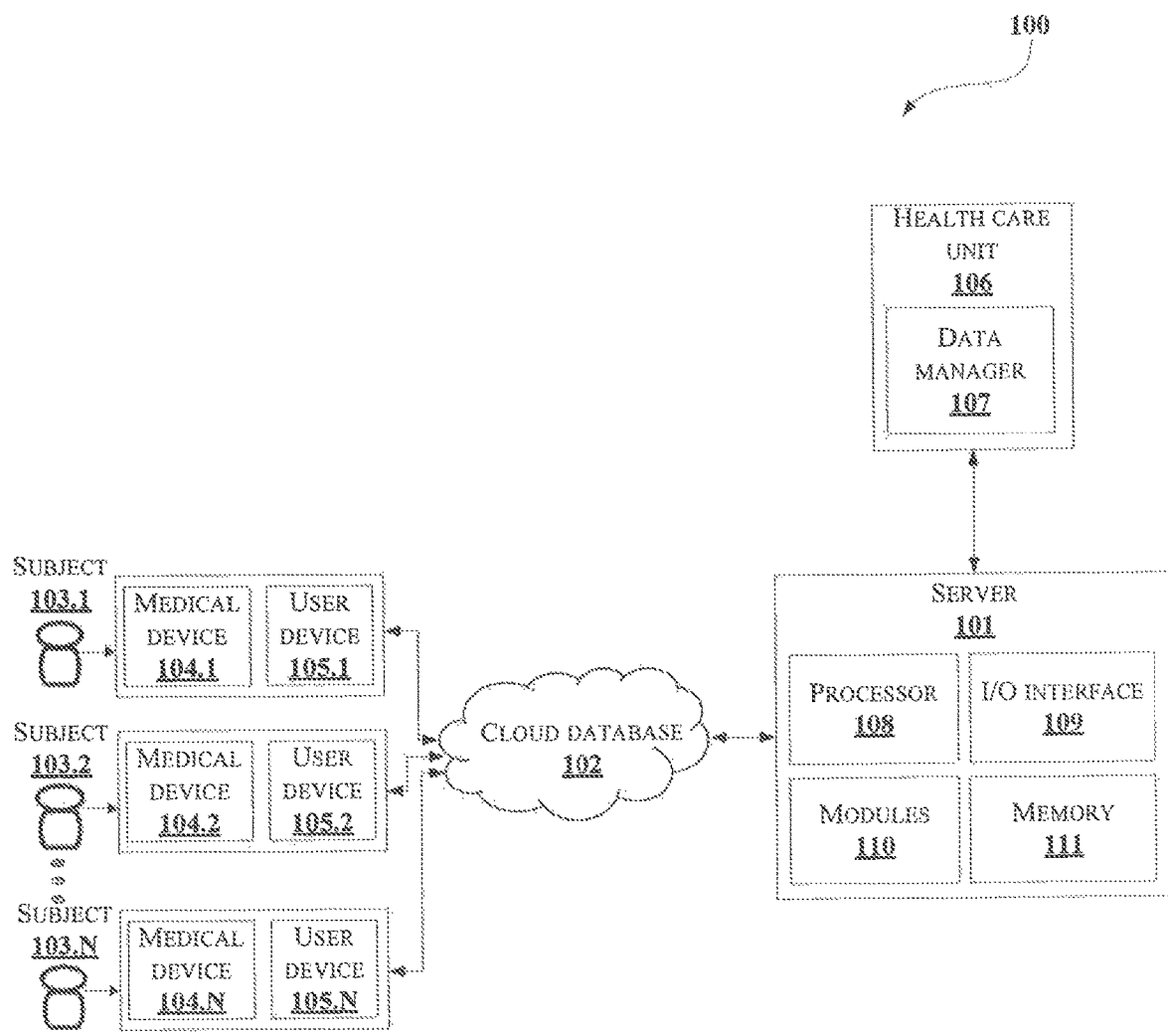
FIGS. 1a and 1b illustrate exemplary embodiments of a system comprising a server for vendor-independent acquisition of medical data by health care unit in accordance with some embodiments of the present disclosure.

It should be appreciated by those skilled in the art that any block diagrams herein represent conceptual views of illustrative systems embodying the principles of the present subject matter. Similarly, it will be appreciated that any flow charts, flow diagrams, state transition diagrams, pseudo code, and the like represent various processes which may be substantially represented in computer readable medium and executed by a computer or processor, whether or not such computer or processor is explicitly shown.

DETAILED DESCRIPTION

In the present document, the word "exemplary" is used herein to mean "serving as an example, instance, or illustration." Any embodiment or implementation of the present subject matter described herein as "exemplary" is not necessarily to be construed as preferred or advantageous over other embodiments.

While the disclosure is susceptible to various modifications and alternative forms, specific embodiment thereof has been shown by way of example in the drawings and will be described in detail below. It should be understood, however that it is not intended to limit the disclosure to the particular forms disclosed, but on the contrary, the disclosure is to cover all modifications, equivalents, and alternative falling within the scope of the disclosure.

The terms "comprises", "comprising", or any other variations thereof, are intended to cover a non-exclusive inclusion, such that a setup, device or method that comprises a list of components or steps does not include only those components or steps but may include other components or steps not expressly listed or inherent to such setup or device or method. In other words, one or more elements in a system or apparatus proceeded by "comprises . . . a" does not, without more constraints, preclude the existence of other elements or additional elements in the system or apparatus.

In the following detailed description of the embodiments of the disclosure, reference is made to the accompanying drawings that form a part hereof, and in which are shown by way of illustration specific embodiments in which the disclosure may be practiced. These embodiments are described in sufficient detail to enable those skilled in the art to practice the disclosure, and it is to be understood that other embodiments may be utilized and that changes may be made without departing from the scope of the present disclosure. The following description is, therefore, not to be taken in a limiting sense.

The present disclosure provides a simple system implementing a server for vendor-independent acquisition of medical data by health care unit associated with the server from one or more medical devices in multiple POCT. The one or more medical devices may be manufactured by different vendors. The system eliminates the need for vendor support for the acquisition of the medical data from each of the one or more medical devices. The present disclosure implements the server along with a cloud database by which the acquisition, independent of the vendor, is achieved. The POCRG interface may be implemented at the server with a data manager of the health care unit and the medical data is provided to the health care unit through Data Message Layer (DML) communication session established due to the implemented POCRG interface. Here, the server is configured to virtualize each of the POCRG in a system with the one or more medical devices in multiple POCT. Upon receiving the medical data, the server implements the POCRG interface for the one or more medical devices and thereby establishes the DML communication session with the data manager of the health care unit. Further, the server transmits the medical data to the data manager through the established DML communication session for achieving the vendor-independent acquisition of the medical data.

Figure 1B:
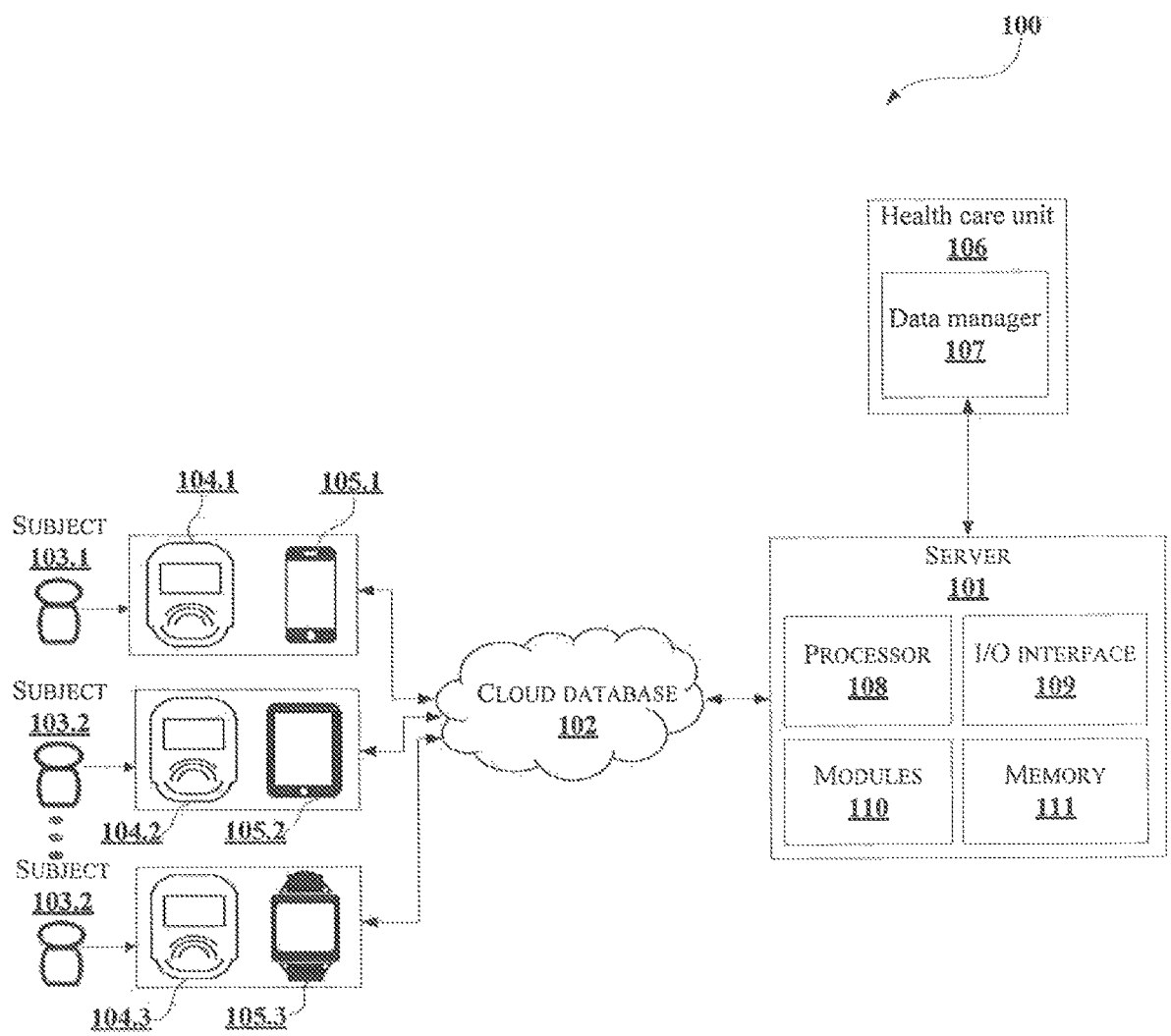

FIGS. 1a and 1b illustrates exemplary embodiments of a system 100 comprising a server 101 for vendor-independent acquisition of medical data by health care unit 106 in accordance with some embodiments of the present disclosure.

The system 100 comprises a server 101, a cloud database 102, one or more subjects 103.1 . . . 103.N (herein collectively referred to as one or more subjects 103), in one of the embodiments, the subjects 103 may be patients whose diagnosis of the medical data is to be performed. The system 100 further comprises one or more medical devices 104.1 . . . 104.N (herein collectively referred to as one or more medical devices 104) and one or more user devices 105.1 . . . 105.N (herein collectively referred to as one or more user devices 105) which are associated with each of the one or more subjects 103. Further, the system 100 comprises health care unit 106 and a data manager 107 of the health care unit 106 connected to the server 101. One of the embodiments of the present disclosure may include multiple health care units with corresponding data managers and associated servers for vendor-independent acquisition of the medical data from one or more subjects 103. The medical devices 104 may be devices which obtains vital parameters (also referred as medical data) of a subject. The one or more medical devices 104 may be but not limited to glucose meter, anticoagulation testing device, and cholesterol testing device as shown in FIG. 1b. Further, the one or more user devices 105 may be devices which are configured to receive the medical data from the one or more medical devices 104 and transmit the medical data to the cloud database 102. The one or more user devices 105 may be but not limited to a laptop computer, a desktop computer, a Personal Computer (PC), a notebook, a smartphone, a tablet, e-book readers, a server, a network server and a smart watch as shown in FIG. 1b. Also, a communication network (not shown in Figure) may be implemented to provide communication between the cloud database 102 and the server 101. In one embodiment, the communication network may be but not limited to 3G network, 4G network and Wireless Fidelity (Wi Fi) network.

The server 101 in the system 100 comprises a processor 108, an Input/Output (I/O) interface 109, modules 110 and a memory 111. The memory 111 in the server 101 is communicatively coupled to the processor 108. The memory 111 stores processor executable instructions which on execution enable the server 101 to perform the vendor-independent acquisition of the medical data.

In one implementation, the server 101 may be implemented in a variety of computing systems, such as a laptop computer, a desktop computer, a Personal Computer (PC), a notebook, a smartphone, a tablet, e-book readers (e.g., Kindles and Nooks), a network server, and the like.

In the system 100, initially, each of the one or more medical devices 104 is registered with the cloud database 102 and the server 101 to enable the acquisition of the medical data by the server 101. The one or more medical devices 104 are registered by providing medical device data to the cloud database 102 and by providing the medical device data and subject data to the server 101. The subject data comprises details of each of the one or more subjects 103 as per records in the health care unit 106 of the corresponding subject and unique ID assigned to the one or more subjects 103 by the health care unit 106. The medical device data comprises serial number, vendor identification number, model number, manufacturer name and medical device name of each of the one or more medical devices 104. The one or more medical devices 104, in real time, provide the medical data to the cloud database 102 via the one or more user devices 105. In one embodiment, the one or more user devices 105 may obtain the medical data from the one or more medical devices 104 via a mobile application in the one or more user devices 105. The mobile application associated with each of the one or more user devices 105 may be vendor specific and the mobile application is configured to obtain the medical data from the one or more medical devices 104. In a non-limiting embodiment, the one or more user devices 105 obtain the medical data via a bluetooth interface. The server 101 transmits request to the cloud database 102 at predefined intervals of time for acquisition of the medical data. The predefined intervals of time may be one of hourly, daily, weekly and monthly as per the requirements of the health care unit 106. The request transmitted by the server 101 comprises list of the one or more medical devices 104 associated with the one or more subjects 103 of the health care unit 106. The one or more medical devices 104 in the list are the medical devices which are registered with the cloud database 102 and the server 101 and are configured to obtain the medical data from the one or more subjects 103 of the health care unit 106. Further, the server 101 obtains the medical data of the one or more subjects 103 from the cloud database 102 based on the request and correlation performed by the cloud database 102. The correlation is performed between the medical data and the medical device data. Here, the medical data is received by the cloud database 102 from the one or more user devices 105 associated with the one or more subjects 103. Upon receiving the medical data, the server 101 implements a POCRG interface for the one or more medical devices 104 and thereby establish a Device Message Layer (DML) communication session with the data manager 107 of the health care unit 106. Further, the server 101 transmits the medical data to the data manager 107 through the established DML communication session for vendor-independent acquisition of the medical data by health care units.

Figure 2:
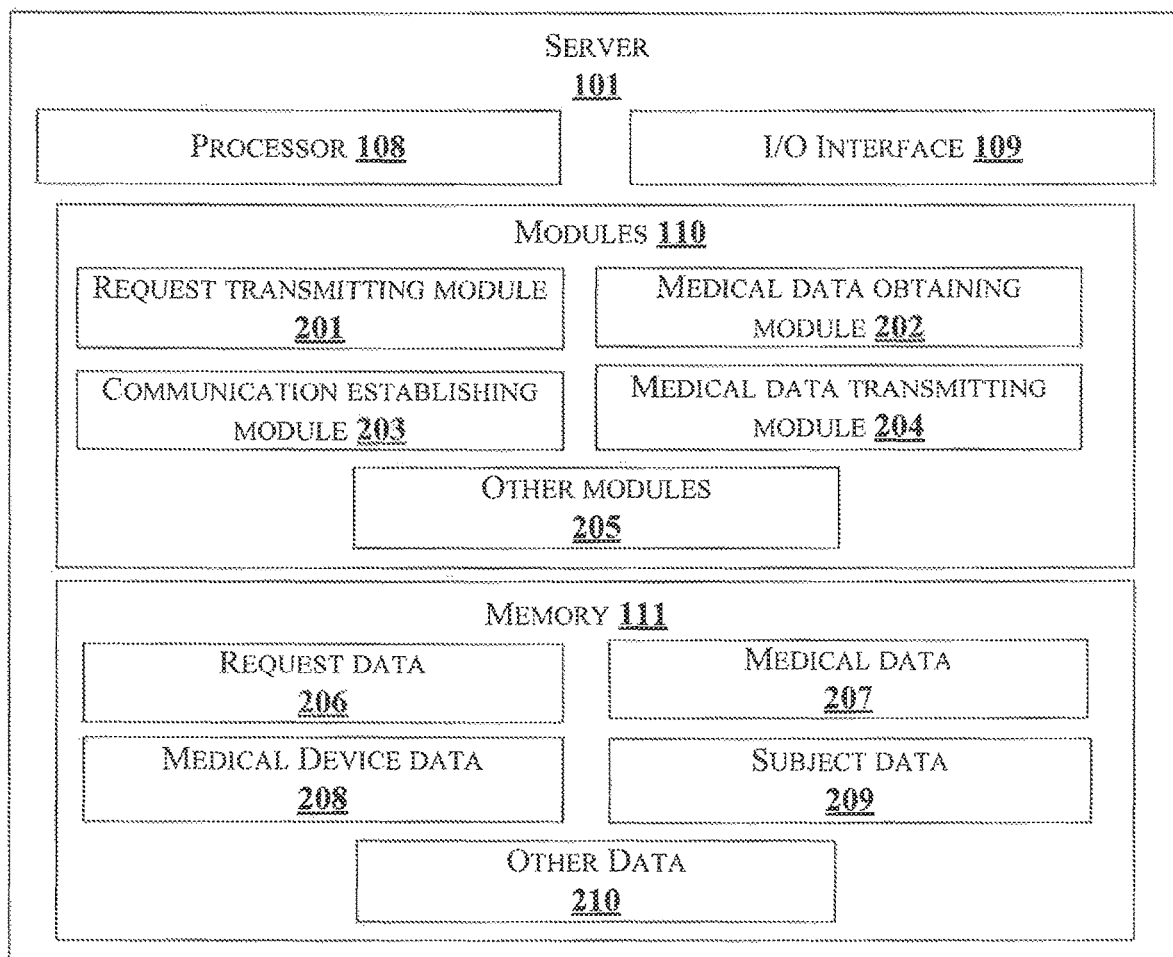
FIG. 2 illustrates a detailed block diagram of a server for vendor-independent acquisition of medical data by health care unit in accordance with some embodiments of the present disclosure.

FIG. 2 illustrates a detailed block diagram of the server 101 for vendor-independent acquisition of medical data by health care unit 106 in accordance with some embodiments of the present disclosure. In the illustrated FIG. 2, the one or more data in the memory 111 and the modules 110 configured in the server 101 are described herein in detail.

In an embodiment, the one or more data in the memory 111 are processed by the modules 110 of the server 101. In one embodiment, the modules 110 may be stored within the memory 111 (not shown in Figure). In an example, the modules 110, communicatively coupled to the processor 108, may also be coupled to the memory 111 and implemented as hardware. As used herein, the term module refers to an application specific integrated circuit (ASIC), an electronic circuit, a field-programmable gate arrays (FPGA), Programmable System-on-Chip (PSoC), a combinational logic circuit, and/or other suitable components that provide the described functionality. The said modules when configured with the functionality defined in the present disclosure invention will result in a novel hardware.

In one implementation, the modules 110 may include, for example, a request transmitting module 201, a medical data obtaining module 202, a communication establishing module 203, a medical data transmitting module 204 and other modules 205 associated with the server 101.

In one embodiment, the one or more data in the memory 111 may include, for example, request data 206 (also referred as request), medical data 207, medical device data 208, subject data 209 and other data 208 associated with the server 101. In one embodiment, the medical data 207, the medical device data 208 and the subject data 209 may be received by the server 101 in real-time via I/O interface 109 for acquisition of the medical data 207. In one embodiment, the request 206 may be transmitted by the server 101 in real time via I/O interface 109 for acquisition of the medical data 207.

Initially, the one or more medical devices 104 are registered with the server 101 to enable the acquisition of the medical data 207 by the server 101. The server 101 acquires the medical data 207 by transmitting the request 206 to the cloud database 102 via the request transmitting module 201 at regular intervals of time. The request 206 comprise list of the one or more medical devices 104 associated with the one or more subjects 103 of the health care unit 106. Further, the medical data obtaining module 202 obtains the medical data 207 of the one or more subjects 103 from the cloud database 102 based on the request 206 and the correlation of the medical data 207 with the medical device data 208 performed by the cloud database 102. Here, the medical data 207 is received by the cloud database 102 from the one or more user devices 105 associated with the one or more subjects 103. Further, the one or more user devices 105 receives the medical data 207 from the one or more associated medical devices 104 of the corresponding one or more subjects 103. Here, the one or more medical devices 104 may be manufactured by different vendors. The one or more user devices 105 comprise a mobile application of the corresponding vendor of the one or more medical devices 104 for receiving the medical data 207. Upon receiving the medical data 207, the server 101 implements the POCRG interface for the one or more medical devices 104 and thereby the communication establishing module 203 establishes the DML communication session with the data manager 107 of the health care unit 106. In one embodiment, the server 101 is associated with a unique thread that assumes identity of one or more medical device 104 for the DML communication. Further, the medical data transmitting module 204 transmits the medical data 207 to the data manager 107 through the established DML communication session for vendor-independent acquisition of the medical data 207 by health care units.

In an embodiment, the other modules 205 of the server 101 may comprise a server application which provides user interfaces for managing the one or more medical devices 104. The server application may enable a user to configure data sync frequency with the cloud database 102 and the data manager 107 which provides time interval for the server 101 to connect with the data manager 107.

In an embodiment, the other modules 205 of the server 101 may comprise a data listener which connects with the cloud database 102 based on a schedule defined by the health care unit 106, shares the request 206 and may request any new medical data if available for the server 101.

In an embodiment, the other modules 205 of the server 101 may comprise a server manager which manages transfer of the medical data 207 to the data manager 107.

In an embodiment, the other modules 205 of the server 101 may comprise individual threads or thread pools which are used for transferring medical data 207 to data manager 107. In a non-limiting embodiment, the data manager 107 may push the medical data 207 to Laboratory Information System (LIS) and Electronic Health Record (EHR) system of the health care unit 106.

Figure 3:
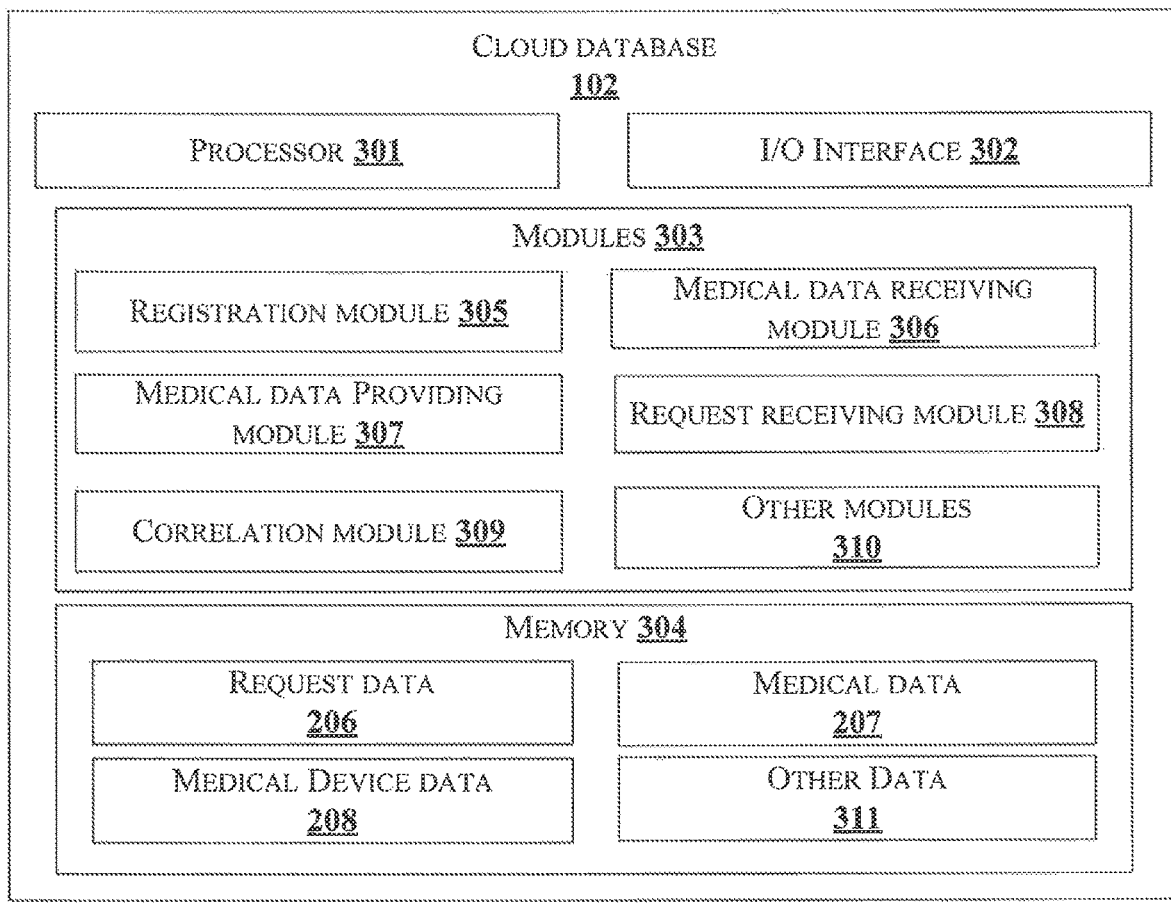
FIG. 3 illustrates a detailed block diagram of a cloud database associated with a server for vendor-independent acquisition of medical data by health care unit in accordance with some embodiments of the present disclosure.

FIG. 3 illustrates a detailed block diagram of the cloud database 102 associated with the server 101 for vendor-independent acquisition of the medical data by the health care unit 107 in accordance with some embodiments of the present disclosure. The one or more data in the memory 304 and the modules 303 configured in the cloud database 102 are described herein in detail.

In an embodiment, the one or more data in the memory 304 are processed by the modules 303 of the cloud database 102. In one embodiment, the modules 303 may be stored within the memory 304 (not shown in Figure). In an example, the modules 303, communicatively coupled to the processor 301, may also be coupled to the memory 304 and implemented as hardware.

In one implementation, the modules 303 may include, for example, registration module 305, medical data receiving module 306, medical data providing module 307, request receiving module 308, correlation module 30 and other modules 310 associated with the cloud database 102.

In one embodiment, the one or more data in the memory 304 may include, for example, the request data 206 (also referred as request 206), the medical data 207, the medical device data 208, and other data 311 associated with the cloud database 102. In one embodiment, the medical data 207 may be transmitted by the cloud database 102 in real-time via I/O interface 302 for acquisition of the medical data 207 by the health care unit 106. In one embodiment, the medical data 207, the medical device data 311 may be received by the cloud database 102 from the one or more user devices 105 in real-time via I/O interface 302 for acquisition of the medical data 207 by the health care unit 106.

Initially, the one or more medical devices 104 are registered with the cloud database 102 via the registration module 305 by providing the medical device data 311 to the cloud database 102. The medical data receiving module 306 receives the medical data 207 from the one or more user devices 105 via a communication network. In an embodiment, the communication network may be but not limited to a wired network, Wi Fi and fiber optic communication.

The correlation module 309 correlates the medical data 207 with the medical device data 208 based on the registration. The medical device data 208 comprises serial number, vendor identification number, model number, manufacturer name and medical device name of each of the one or more medical devices 104. When the cloud database 102 obtains the request 206 via the request receiving module 308 from the server 101, the medical device providing module 307 transmits the medical data 207 based on the correlation and the request 206. Upon receiving the medical data 207, the server 101 implements the POCRG interface for the one or more medical devices 104 and thereby establish the DML communication session with the data manager 107 of the health care unit 106. Further, the server 101 transmits the medical data 207 to the data manager 107 through the established DML communication session for vendor-independent acquisition of the medical data 207 by health care units.

In one embodiment, the other modules 311 of the cloud database 102 may comprise a web service for providing lookup services for the one or more medical devices 104. The lookup services may be based on token associated with the cloud database 102.

In another embodiment, the other modules 311 of the cloud database 102 may comprise admin User Interface (UI) for managing the one or more medical devices 104 and the server 101.

In another embodiment, the other modules 311 of the cloud database 102 may comprise a data management module which manages data such as the medical data 207, the medical device data 208 in the cloud database 102. The data management module may be further configured maintain data queue for each of registered one or more medical devices 104 and provide backend services for transferring the medical data 207 to the server 101. In an embodiment, data queue the medical data 207 for each of the one or more medical devices 104 may be deleted once the medical data 207 is transferred to the server 101.

In another embodiment, the other modules 311 of the cloud database 102 may comprise an application module to manage registration and deregistration of the one or more medical devices 104. Also the application module may track status of the one or more medical devices 104. Further, the application module may maintain the medical device data 208 in the memory 304 associated with the cloud database 102.

Figure 4:
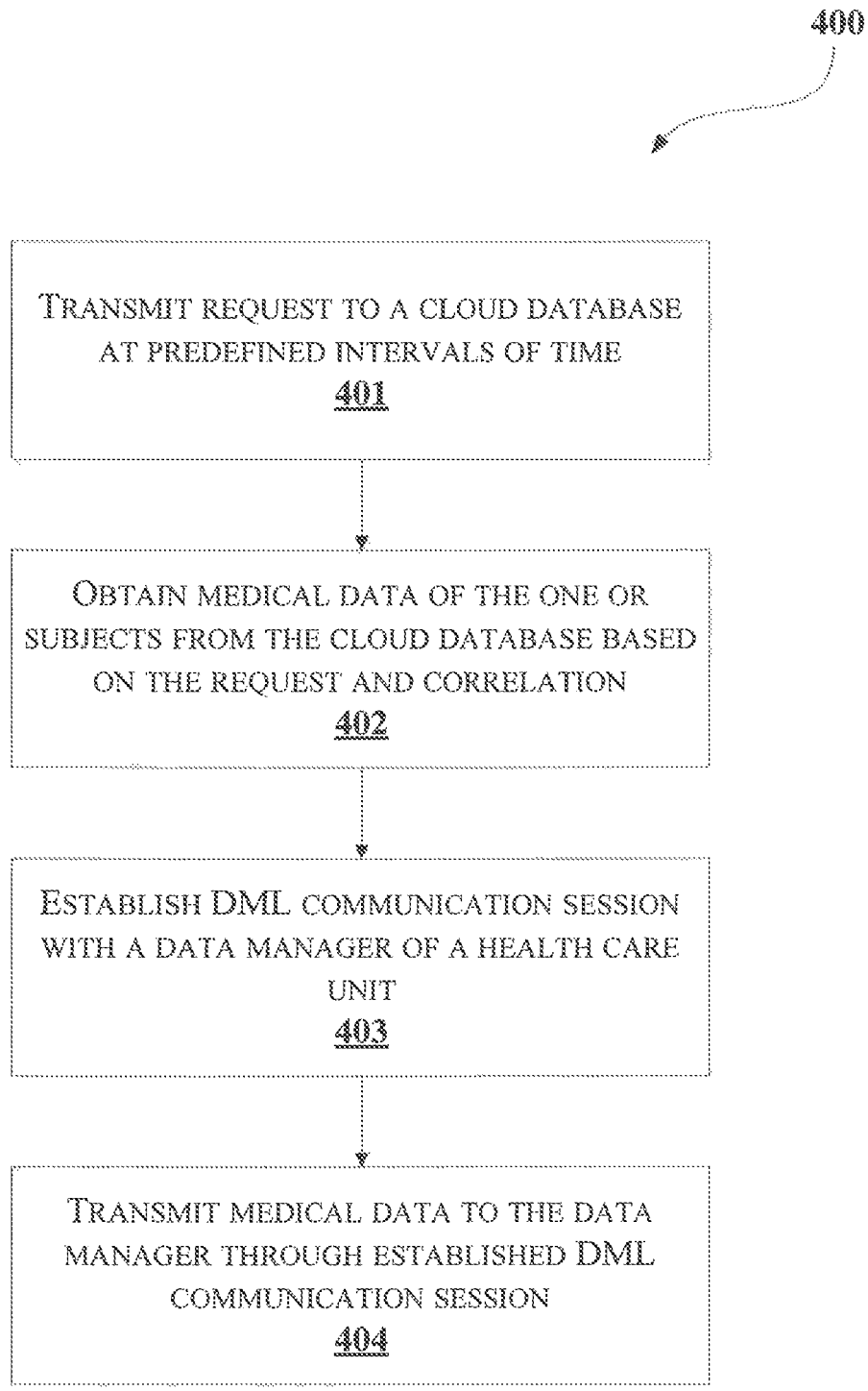
FIG. 4 illustrates a flow diagram showing steps performed by a server for vendor-independent acquisition of medical data by health care unit in accordance with some embodiments of the present disclosure.

FIG. 4 illustrates a flow diagram showing steps performed by the server 101 for vendor-independent acquisition of the 207 medical data by the health care unit 106 in accordance with some embodiments of the present disclosure.

The order in which the method is described is not intended to be construed as a limitation, and any number of the described method blocks can be combined in any order to implement the method. Additionally, individual blocks may be deleted corn the methods without departing from the scope of the subject matter described herein. Furthermore, the method can be implemented in any suitable hardware, software, firmware, or combination thereof.

At block 401, the request transmitting module of the server 101 transmits the request 206 to the cloud database 102 at the predefined intervals of time. The request 206 comprises comprise list of the one or more medical devices 104 associated with the one or more subjects 103 of the health care unit 106.

At block 402, the medical data obtaining module 202 of the server 101 obtains the medical data 207 of the one or more subjects 103 from the cloud database 102 based on the request 206 and the correlation. The correlation is performed by the cloud database 102 between the medical data 207 and the medical device data 208.

At block 403, the communication establishing module 204 of the server 101 establishes DML communication session with the data manager 107 of the health care unit 106. The server 101 implements the POCRG interface for the one or more medical devices 104 for establishing the DML communication session.

At block 404, the medical data transmitting module 204 of the server 101, transmits medical data 207 to the data manager 107 through the established DML communication session. The received medical data is stored and processed in the data manger 107 as per the requirements of the health care unit 106.

Figure 5:
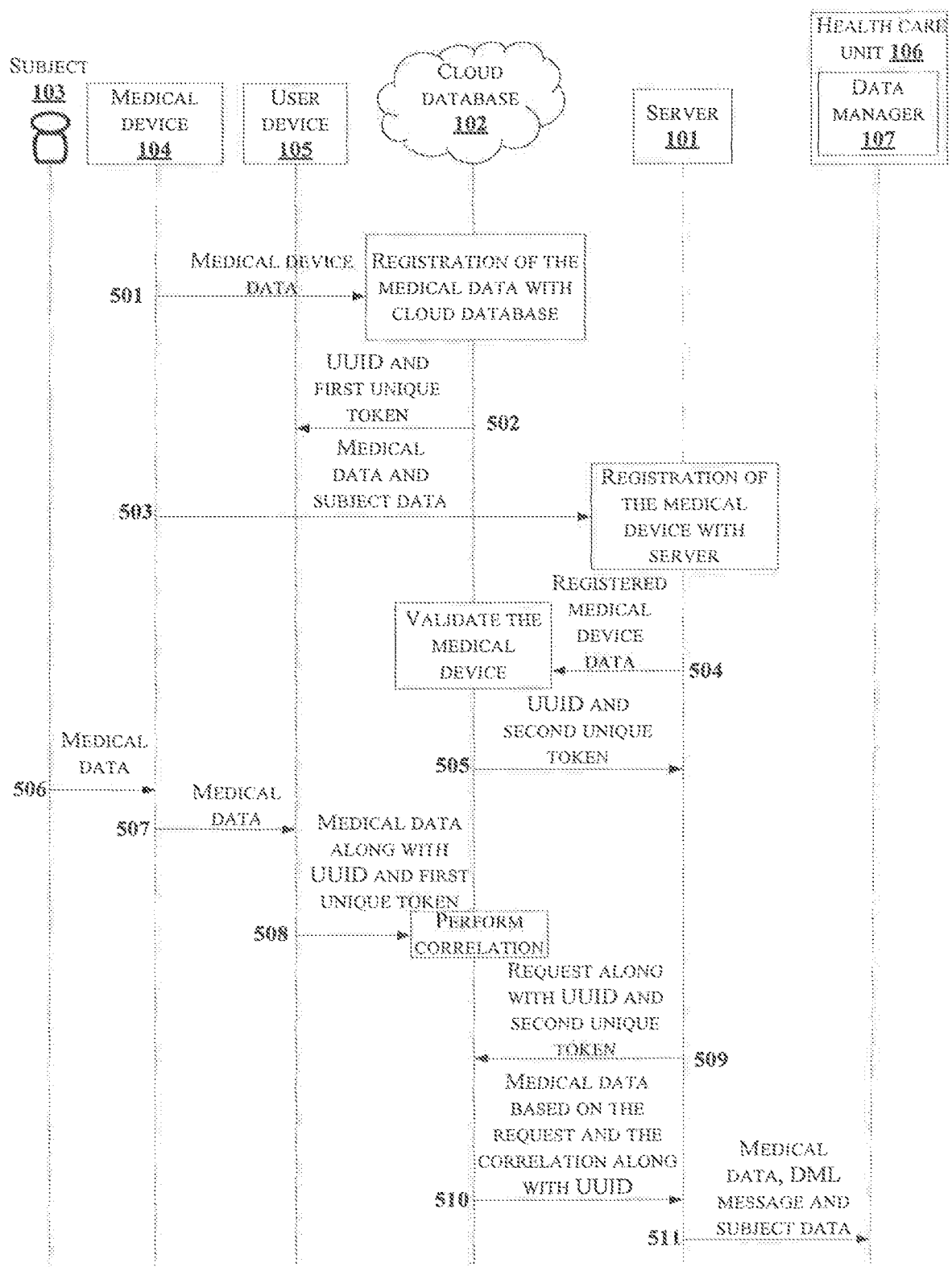
FIG. 5 illustrates a sequential diagram of a system implementing a server for vendor-independent acquisition of medical data by health care unit in accordance with some embodiments of the present disclosure.

FIG. 5 illustrates a sequential diagram of the system 100 implementing the server 101 for vendor-independent acquisition of the medical data 207 by the health care unit 106 in accordance with some embodiments of the present disclosure.

Consider a scenario for acquisition of the medical data 207 of a subject 103, associated with a health care unit 106 with a data manager 107, is to be performed. A medical device 104 connected to a user device 105 is associated with the subject 103 for obtaining the medical data 207 of the subject 103.

Initially, at step 501, registration of the medical device 104 with the cloud database 102 and the server 101 is performed. The medical device 104 provides the medical device data 208 to the cloud database 102 for registration with the cloud database 102. The medical device data 208 comprises of serial number, vendor identification number, model number, manufacturer name and medical device name of the mobile device 104. Upon performing the registration of the medical device 104, at step 502, the cloud database 102 acknowledges the medical device 104 by transmitting Universal Unique Identifier (UUID) and a first unique token to the medical device 104. In one embodiment, the UUID is issued based on the medical devices data 207.

Further, at step 503, for registration of the medical device 104 with the server 101, the medical device data 208 and the subject data 209 is provided to the server 101 for the registration. In one embodiment, the medical device data 208 and the subject data 209 may be entered manually to the server 101 for the registration. The subject data 209 comprises details of the subject 103 as per records in the health care unit 106 of the subject 103 and unique ID assigned to the subject 103 by the health care unit 106.

Upon performing the registration of the medical device 104, the server 101 provides the medical device data 311 of the registered medical device 104 to the cloud database 102 for validation at step 504. The cloud database 102, upon receiving said medical data 207, performs validation. The validation includes checking if the medical devices 104 to be registered with the server 101 already registered with the cloud database 102. In one embodiment, the cloud database 102 matches the medical device data 311 shared by the server 101 with the medical device data 311 of the medical device 104 registered with the cloud database. Upon, the validation, at step 505, the cloud database 102 forwards the UUID and a second unique token to the server 101. In one embodiment, the second unique token may be the first unique token with a predefined prefix.

At step 506, the medical data 207 may be obtained by the medical device 104 in real time from the subject 103. At step 507, the received medical data 207 is forwarded to the cloud database 102 via the user device 105. At stop 508, the medical data 207 sent to the cloud database 102 is transmitted along with the UUID and the first unique token to the cloud database 102 by the user device 105. Upon receiving the medical data 207 by the cloud database 102, the cloud database 102 performs correlation of the medical data 207 with the medical device data 311. In one embodiment, the correlation includes mapping of the medical data 207 with the medical device data 311 to provide information regarding the medical device 104 associated with the medical data 207.

For the acquisition of the medical data 207, at step 509, the server 101 transmits request 312 along with the UUID and the second unique token to the cloud database 102. The request 312 comprises list of medical devices whose medical data 207 is to be obtained by the health care unit 106. The request 312 is sent at predefined intervals of time by the server 101 based on the requirements of the health care unit 106. Upon receiving the request 312, at step 510, the cloud database 102 provides the medical data 207 to the server 101 based on the request 312 and the correlational along with the UUID. Further, at step 511, the server 101 forwards the medical data 207 along with DML message and the subject data 209 to the data manager 107 of the health care unit 106. The server 101 may store and process the medical data 207. The processed medical data may be used for the diagnosis of the subject 103. In one embodiment, at least one of the UUID, the first unique token and the second unique token may be provided and received for enabling identity and authentication in the system 100. In one embodiment, the first unique token and the second unique token may not be duplication.

Computer System

Figure 6:
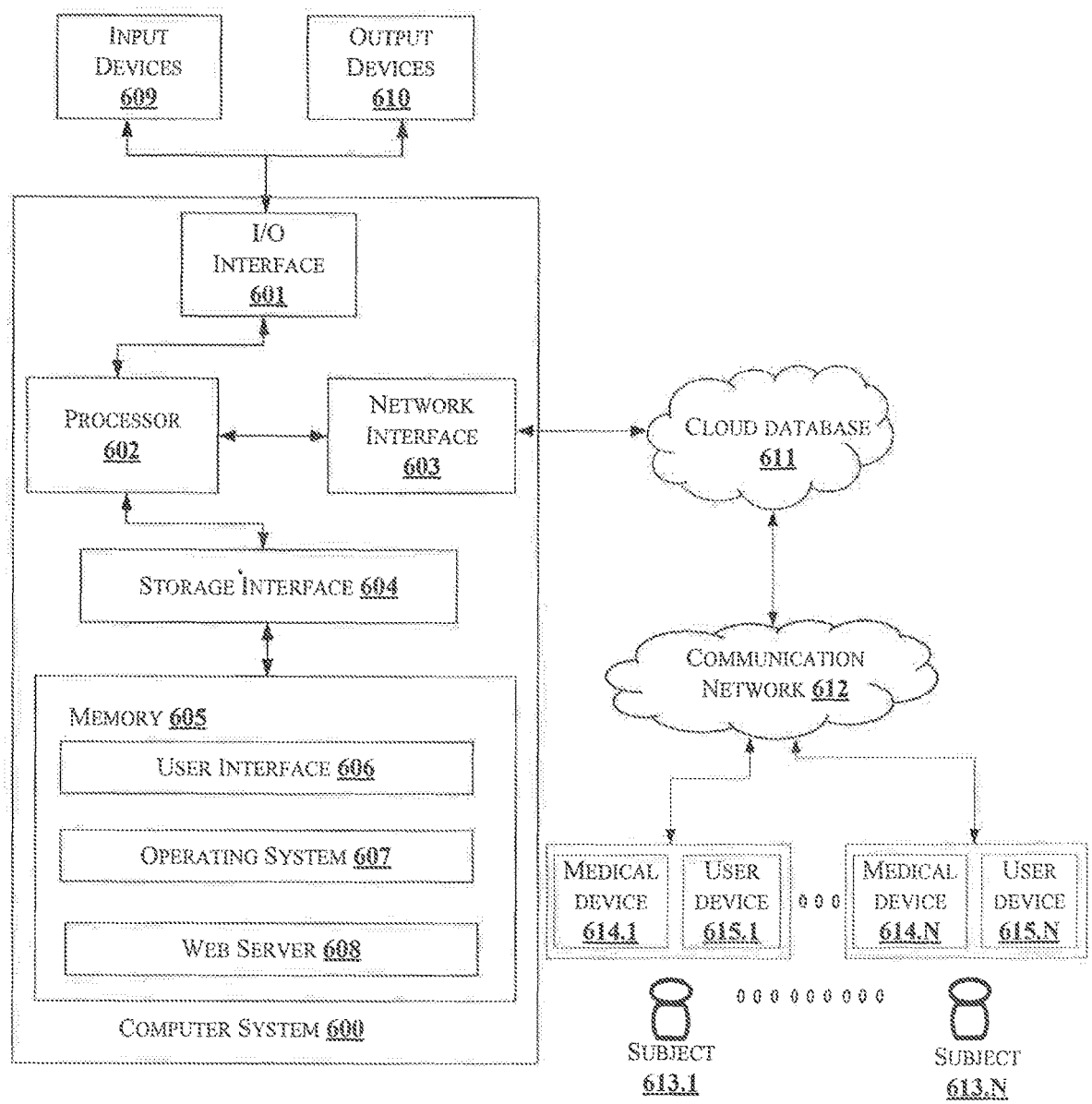
FIG. 6 illustrates a block diagram of an exemplary computer system for implementing some embodiments consistent with the present disclosure.

FIG. 6 illustrates a block diagram of an exemplary computer system for implementing some embodiments consistent with the present disclosure.

In an embodiment, the computer system 600 is used to implement the server 601. The computer system 600 may comprise a central processing unit ("CPU" or "processor") 602. The processor 602 may comprise at least one data processor for executing program components for managing the performance of at least one instrumentation device deployed across one or more sites. The processor 602 may include specialized processing units such as integrated system (bus) controllers, memory management control units, floating point units, graphics processing units, digital signal processing units, etc.

The processor 602 may be disposed in communication with one or more input/output (I/O) devices (not shown) via I/O interface 601. The I/O interface 601 may employ communication protocols/methods such as, without limitation, audio, analog, digital, monoaural, RCA, stereo, IEEE-1394, serial bus, universal serial bus (USB), infrared, PS/2, BNC, coaxial, component, composite, digital visual interface (DVI), high-definition multimedia interface (HDMI), RF antennas, S-Video, VGA, IEEE 802.n/b/g/n/x, Bluetooth, cellular (e.g., code-division multiple access (CDMA), high-speed packet access (HSPA+), global system for mobile communications (GSM), long-term evolution (LTE), WiMax, or the like), etc.

Using the I/O interface 601, the computer system 600 may communicate with one or more I/O devices. For example, the input device 603 may be an antenna, keyboard, mouse, joystick, (infrared) remote control, camera, card reader, fax machine, dongle, biometric reader, microphone, touch screen, touchpad, trackball, stylus, scanner, storage device, transceiver, video device/source, etc. The output device 610 may be a printer, fax machine, video display (e.g., cathode ray tube (CRT), liquid crystal display (LCD), light-emitting diode (LED), plasma, Plasma display panel (PDP), Organic light-emitting diode display (OLED) or the like), audio speaker, etc.

In some embodiments, the computer system 600 is connected to a cloud database 611 through communication network which may be but not limited to a wired network, Wi Fi network and so on. In one embodiment, the cloud database 611 is further connected to one or more medical devices 614.1, . . . 614.N and the corresponding one or more user devices 615.1 . . . 615.N associated with one or more subjects 613.1 . . . 613 via a communication network 612. The processor 602 may be disposed in communication with the communication network 612 via a network interface 603. The network interface 603 may communicate with the communication network 610. The network interface 603 may employ connection protocols including, without limitation, direct connect, Ethernet ((e.g., twisted pair 10/100/1000 Base T), transmission control protocol/internet protocol (TCP/IP), token ring, IEEE 802.11a/b/g/n/x, etc. The communication network 610 may include, without limitation, a direct interconnection, local area network (LAN), wide area network (WAN), wireless network (e.g., using Wireless Application Protocol), the Internet, etc. Using the network interface 603 and the communication network 611, the computer system 600 may communicate with the plurality of mobile devices 612. The network interface 603 may employ connection protocols include, but not limited to, direct connect, Ethernet (e.g., twisted pair 10/100/1000 Base T), transmission control protocol/internet protocol (TCP/IP), token ring, IEEE 802.11a/b/g/n/x, etc.

The communication network 610 includes, but is not limited to, a direct interconnection, an e-commerce network, a peer to peer (P2P) network, local area network (LAN), wide area network (WAN), wireless network (e.g., using Wireless Application Protocol), the Internet, Wi-Fi and such. The first network and the second network may either be a dedicated network or a shared network, which represents an association of the different types of networks that use a variety of protocols, for example, Hypertext Transfer Protocol (HTTP), Transmission Control Protocol/Internet Protocol (TCP/IP), Wireless Application Protocol (WAP), etc., to communicate with each other. Further, the first network and the second network may include a variety of network devices, including routers, bridges, servers, computing devices, storage devices, etc.

In some embodiments, the processor 602 may be disposed in communication with a memory 605 (e.g., RAM, ROM, etc. not shown in FIG. 6) via a storage interface 604. The storage interface 604 may connect to the memory 605 including, without limitation, memory drives, removable disc drives, etc., employing connection protocols such as serial advanced technology attachment (SATA), Integrated Drive Electronics (IDE), IEEE4394, Universal Serial Bus (USB), fiber channel, Small Computer Systems Interface (SCSI), etc. The memory drives may further include a drum, magnetic disc drive, magneto-optical drive, optical drive, Redundant Array of Independent Discs (RAID), solid-state memory devices, solid-state drives, etc.

The memory 605 may store a collection of program or database components, including, without limitation, user interface 606, an operating system 607, web server 608 etc. In some embodiments, computer system 600 may store user/application data (not shown in figure), such as the data, variables, records, etc. as described in this disclosure. Such databases may be implemented as fault-tolerant, relational, scalable, secure databases such as Oracle or Sybase.

The operating system 607 may facilitate resource management and operation of the computer system 600. Examples of operating systems include, without limitation, Apple Macintosh OS X, Unix, Unix-like system distributions (e.g., Berkeley Software Distribution (BSD), FreeBSD, NetBSD, OpenBSD, etc.), Linux distributions (e.g., Red Hat, Ubuntu, Kubuntu, etc.), IBM OS/2, Microsoft Windows (XP, Vista/7/8, etc.), Apple iOS, Google Android, Blackberry OS, or the like.

In some embodiments, the computer system 600 may implement a web browser 608 stored program component. The web browser 608 may be a hypertext viewing application, such as Microsoft Internet Explorer, Google Chrome, Mozilla Firefox, Apple Safari, etc. Secure web browsing may be provided using Secure Hypertext Transport Protocol (HTTPS), Secure Sockets Layer (SSL), Transport Layer Security (TLS), etc. Web browsers 608 may utilize facilities such as AJAX, DHTML, Adobe Flash, JavaScript, Java, Application Programming Interfaces (APIs), etc. In some embodiments, the computer system 600 may implement a mail server stored program component. The mail server may be an Internet mail server such as Microsoft Exchange, or the like. The mail server may utilize facilities such as ASP, ActiveX, ANSI C++/C#, Microsoft .NET, CGI scripts, Java, JavaScript, PERL, PHP, Python, WebObjects, etc. The mail server may utilize communication protocols such as Internet Message Access Protocol (IMAP), Messaging Application Programming interface (MAPI), Microsoft Exchange, Post Office Protocol (POP), Simple Mail Transfer Protocol (SMTP), or the like. In some embodiments, the computer system. 600 may implement a mail client stored program component. The mail client may be a mail viewing application, such as Apple Mail, Microsoft Entourage, Microsoft Outlook, Mozilla Thunderbird, etc.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include Random Access Memory (RAM), Read-Only Memory (ROM), volatile memory, nonvolatile memory, hard drives, CD ROMs, DVDs, flash drives, disks, and any other known physical storage media.

Embodiments of the present disclosure less complex system for acquisition of medical data by the health care units.

Embodiments of the present disclosure provide a server to reduce overall effort for integration of POCTRG with the data manager of a health care unit.

Embodiment of the present disclosure solves interoperability involved in the integration of the POCTRG with data manager as it is based on industry standard.

The described operations may be implemented as a method, system or article of manufacture using standard programming and/or engineering techniques to produce software, firmware, hardware, or any combination thereof. The described operations may be implemented as code maintained in a "non-transitory computer readable medium", where a processor may read and execute the code from the computer readable medium. The processor is at least one of a microprocessor and a processor capable of processing and executing the queries. A non-transitory computer readable medium may comprise media such as magnetic storage medium (e.g., hard disk drives, floppy disks, tape, etc), optical storage (CD-ROMs, DVDs, optical disks, etc.), volatile and non-volatile memory devices (e.g., EEPROMs, ROMs, PROMs, RAMS, DRAMs, SRAMs, Flash Memory, firmware, programmable logic, etc.), etc. Further, non-transitory computer-readable media comprise all computer-readable media except for a transitory. The code implementing the described operations may further be implemented in hardware logic (e.g., an integrated circuit chip, Programmable Gate Array (PGA), Application Specific Integrated Circuit (ASIC), etc.).

Still further, the code implementing the described operations may be implemented in "transmission signals", where transmission signals may propagate through space or through a transmission media, such as an optical fiber, copper wire, etc. The transmission signals in which the code or logic is encoded may further comprise a wireless signal, satellite transmission, radio waves, infrared signals, Bluetooth, etc. The transmission signals in which the code or logic is encoded is capable of being transmitted by a transmitting station and received by a receiving station, where the code or logic encoded in the transmission signal may be decoded and stored in hardware or a non-transitory computer readable medium at the receiving and transmitting stations or devices. An "article of manufacture" comprises non-transitory computer readable medium, hardware logic, and/or transmission signals in which code may be implemented. A device in which the code implementing the described embodiments of operations is encoded may comprise a computer readable medium or hardware logic. Of course, those skilled in the art will recognize that many modifications may be made to this configuration without departing from the scope of the invention, and that the article of manufacture may comprise suitable information bearing medium known in the art.

The terms "an embodiment", "embodiment", "embodiments", "the embodiment", "the embodiments", "one or more embodiments", "some embodiments", and "one embodiment" mean "one or more (but not all) embodiments of the invention(s)" unless expressly specified otherwise.

The terms "including", "comprising", "having" and variations thereof mean "including but not limited to", unless expressly specified otherwise.

The enumerated listing of items does not imply that any or all of the items are mutually exclusive, unless expressly specified otherwise.

The terms "a", "an" and "the" mean "one or more", unless expressly specified otherwise.

A description of an embodiment with several components in communication with each other does not imply that all such components are required. On the contrary a variety of optional components are described to illustrate the wide variety of possible embodiments of the invention.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article or a different number of devices/articles may be used instead of the shown number of devices or programs. The functionality and/or the features of a device may be alternatively embodied by one or more other devices which are not explicitly described as having such functionality/features. Thus, other embodiments of the invention need not include the device itself.

The illustrated operations of FIG. 4 show certain events occurring in a certain order. In alternative embodiments, certain operations may be performed in a different order, modified or removed. Moreover, steps may be added to the above described logic and still conform to the described embodiments. Further, operations described herein may occur sequentially or certain operations may be processed in parallel. Yet further, operations may be performed by a single processing unit or by distributed processing units.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based here on. Accordingly, the disclosure of the embodiments of the invention is intended to be illustrative, but not limiting, of the scope of the invention, which is set forth in the following claims.

While various aspects and embodiments have been disclosed herein, other aspects and embodiments will be apparent to those skilled In the art. The various aspects and embodiments disclosed herein are for purposes of illustration and are not intended to be limiting, with the true scope and spirit being indicated by the following claims.

| Referral Numerals: | |
| --- | --- |
| Reference Number | Description |
| 100 | System |
| 101 | Server |
| 102 | Cloud Database |
| 103.1 ... 103.N | Subjects |
| 104.1 ... 104.N | Medical Devices |
| 105.1 ... 105.N | User Devices |
| 106 | Health Care Unit |
| 107 | Data Manager |
| 108 | Processor |
| 109 | I/O Interface |
| 110 | Modules |
| 111 | Memory |
| 201 | Request Transmitting Module |
| 202 | Medical Data Obtaining Module |
| 203 | Communication Establishing Module |
| 204 | Medical Data Transmitting Module |
| 205 | Other Modules |
| 206 | Request Data |
| 207 | Medical Data |
| 208 | Medical Device Data |
| 209 | Subject Data |
| 210 | Other Data |
| 301 | Processor |
| 302 | I/O Network |
| 303 | Modules |
| 304 | Memory |
| 305 | Registration Module |
| 306 | Medical Data Receiving Module |
| 307 | Medical Data Providing Module |
| 308 | Request Receiving Module |
| 309 | Correlation Module |
| 310 | Other Modules |
| 311 | Other Data |
| 600 | Computer System |
| 601 | I/O Interface |
| 602 | Processor |
| 603 | Network Interface |
| 604 | Storage Interface |
| 605 | Memory |
| 606 | User Interface |
| 607 | Operating System |
| 608 | Web Server |
| 609 | Input Devices |
| 610 | Output Devices |
| 611 | Cloud Database |
| 612 | Communication Network |
| 613.1 ... 613.N | Subjects |
| 614.1 ... 614.N | Medical Devices |
| 615.1 ... 615.N | User Devices |

I claim:

1. A method for vendor-independent acquisition of medical data by health care units, comprising:

transmitting, by a server associated with a health care unit, a request to a cloud database at predefined intervals of time, wherein the request comprises a list of one or more medical devices associated with one or more subjects' of the health care unit;

obtaining, by the server, medical data of the one or more subjects from the cloud database based on the request and correlation, performed by the cloud database, of the medical data with medical device data, wherein the cloud database receives the medical data from one or more user devices associated with the one or more subjects;

establishing, by the server, a Device Message Layer (DML) communication session with a data manager of the health care unit, wherein establishing the DML communication session comprises implementing a Point of Care Report Generator (POCRG) interface for the one or more medical devices, and wherein the server virtualizes each of the POCRG interface in a system with the one or more medical devices in multiple Point of Care Testing (POCT), and wherein the POCRG interface implements a POCT1-A2 protocol for exchange of the medical data between the data manager and the one or more medical devices in the multiple POCT; and transmitting, by the server, the medical data to the data manager through the established DML communication session for vendor-independent acquisition of the medical data by health care units.

2. The method as claimed in claim 1, wherein the one or more user devices receives the medical data from the one or more associated medical devices of the corresponding one or more subjects, manufactured by vendors, using a mobile application of the corresponding vendor of the one or more medical devices.

3. The method as claimed in claim 1, wherein the one or more medical devices are registered with the cloud database and the server by providing at least one of the medical device data and subject data.

4. The method as claimed in claim 3, wherein the cloud database correlates the medical data with the medical device data based on the registration.

5. The method as claimed in claim 3, wherein the subject data comprises details of each of the one or more subjects as per records in the health care unit of the subject and unique ID assigned to the one or more subjects by the health care unit.

6. The method as claimed in claim 1, wherein the medical device data comprises serial number, vendor identification number, model number, manufacturer name and medical device name of each of the one or more medical devices.

7. A server for vendor-independent acquisition of medical data by health care units, comprises:
a processor; and
a memory communicatively coupled to the processor, wherein the memory stores processor-executable instructions, which, on execution, cause the processor to:

transmit a request to a cloud database at predefined intervals of time, wherein the request comprises a list of one or more medical devices associated with one or more subjects of the health care unit;

obtain medical data of the one or more subjects from the cloud database based on the request and correlation, performed by a cloud database, of the medical data with medical device data, wherein the cloud database receives the medical data from one or more user devices associated with the one or more subjects;

establish a Device Message Layer (DML) communication session with a data manager of the health care unit, wherein establishing the DML communication session comprises implementing a Point of Care Report Generator (POCRG) interface for the one or more medical devices, and wherein the server virtualizes each of the POCRG interface in a system with the one or more medical devices in multiple Point of Care Testing (POCT), and wherein the POCRG interface implements a POCT1-A2 protocol for exchange of the medical data between the data manager and the one or more medical devices in the multiple POCT; and transmit the medical data to the data manager through the established DML communication session for vendor-independent acquisition of the medical data by health care units.

8. The server as claimed in claim 7, wherein the one or more user devices receives the medical data from the one or more associated medical devices of the corresponding one or more subjects, manufactured by vendors, using a mobile application of the corresponding vendor of the one or more medical devices.

9. The server as claimed in claim 7, wherein the one or more medical devices are registered with the cloud database and the server by providing at least one of the medical device data and subject data.

10. The server as claimed in claim 9, wherein the cloud database correlates the medical data with the medical device data based on the registration.

11. The server as claimed in claim 9, wherein the subject data comprises details of each of the one or more subjects as per records in the health care unit of the subject and unique ID assigned to the one or more subjects by the health care unit.

12. The server as claimed in claim 7, wherein the medical device data comprises serial number, vendor identification number, model number, manufacturer name and medical device name of each of the one or more medical devices.

* * * * *